US008684993B2

(12) United States Patent
Haindl

(10) Patent No.: US 8,684,993 B2
(45) Date of Patent: Apr. 1, 2014

(54) DEVICE FOR CONNECTING A TUBULAR PART TO THE INSIDE OF A BOTTLE

(76) Inventor: Hans Haindl, Wennigsen (DE)

( * ) Notice: Subject to any disclaimer, the term of this patent is extended or adjusted under 35 U.S.C. 154(b) by 114 days.

(21) Appl. No.: 12/966,675

(22) Filed: Dec. 13, 2010

(65) Prior Publication Data

US 2011/0245797 A1 Oct. 6, 2011

Related U.S. Application Data

(63) Continuation of application No. 11/715,934, filed on Mar. 9, 2007, now abandoned, which is a continuation of application No. PCT/EP2005/009536, filed on Sep. 6, 2005.

(30) Foreign Application Priority Data

Sep. 10, 2004 (DE) ........................ 10 2004 044 288

(51) Int. Cl.
*A61B 19/00* (2006.01)

(52) U.S. Cl.
USPC ............ 604/415; 604/411; 604/414; 604/416

(58) Field of Classification Search
USPC .......................... 604/403, 411, 414, 415, 416
See application file for complete search history.

(56) References Cited

U.S. PATENT DOCUMENTS

| | | | | |
|---|---|---|---|---|
| 2,342,215 | A * | 2/1944 | Perelson | 215/247 |
| 5,772,652 | A * | 6/1998 | Zielinski | 604/411 |
| 6,070,623 | A * | 6/2000 | Aneas | 141/329 |
| 6,572,592 | B1 * | 6/2003 | Lopez | 604/256 |

* cited by examiner

*Primary Examiner* — Leslie Deak
(74) *Attorney, Agent, or Firm* — Shlesinger, Arkwright & Garvey LLP

(57) ABSTRACT

Device for connecting a tubular part having a first end provided with a tip, and a second end provided with a connecting device. The connecting device connects an inside of the tubular part with a syringe and with the inside of a bottle, which bottle includes a neck having a stopper penetrable by the tip of the tubular part. Device includes a supporting device for sealing and fitting the device into place on the neck of the bottle in a tight and substantially centered manner. A holding device holds the tubular part in a displaceable manner relative to the supporting device in a penetration direction of the tip of the tubular part. Holding device includes a tight, deformable membrane with two edges, one edge of which is connected tightly to the tubular part and another edge of which is connected tightly to the supporting device.

17 Claims, 7 Drawing Sheets

DEVICE FOR CONNECTING A TUBULAR PART TO THE INSIDE OF A BOTTLE

CROSS-REFERENCE TO RELATED APPLICATIONS

This application is a continuation of application Ser. No. 11/715,934, filed Mar. 9, 2007, which application Ser. No. 11/715,934 is a continuation of application no. PCT/EP2005/009536, filed Sep. 6, 2005, which claims the priority of German application no. 10 2004 044 288.6, filed Sep. 10, 2004, and each of which is incorporated herein by reference.

FIELD OF THE INVENTION

The invention relates to a device for connecting a tubular part to the inside of a bottle, and which bottle includes a neck provided with a stopper which can be penetrated by the tip of the tubular part.

BACKGROUND OF THE INVENTION

To remove a medical fluid from a bottle sealed with a stopper that can be penetrated, it is generally known to use a hollow needle connected to a syringe to penetrate the stopper, insert the needle into the fluid, and draw the fluid into the syringe. In doing so, there exists the danger of puncture wounds, this danger being particularly great when lay medical workers in the private sector are handling the syringe. To avoid this danger, devices generally known as transfer and removal systems are known that permit needleless operation and thus protect the user from puncture wounds.

A device is known from U.S. Pat. No. 6,706,031 B2 in which a disk, which surrounds the tubular part and can be displaced within a cylindrical space, forms a guide device to laterally guide the tubular part. This does not result in parallel guiding in the penetration direction, which occurs only when a syringe has been put into position on the connecting device on the second, rear end of the tubular part. After the cylindrical body of the syringe has been put into position on the connecting device, it enters a cylindrical housing part of the device, and thereby forms a second lateral guide with the result that the tubular part as a unit is guided in the penetration direction. The design is expensive and cannot be used with all types of syringes.

Similar complicated devices are known from the European patent specifications EP 1 150 639 B1 and EP 1 006 981 B1. They all have the disadvantage that they include a plurality of parts, so that their manufacture and assembly is lavish and expensive.

A device of the type which includes a device for connecting a tubular part, a first end of which is provided with a tip, and a second end of which is provided with connecting device for connecting the inside of the tubular part to a syringe, and wherein the holding device is formed by elastic tongues, which are deformable in a direction parallel to the penetration direction in order to escort the motion of the piston in the penetration direction, is known from DE 600 04 082 T2. A piston, which can slide within the internal bore of a sleeve disposed on the supporting device, which is adjacent to the neck of the bottle, is provided to guide the tubular part. This known device is complicated and lavish and therefore also expensive.

OBJECTS AND SUMMARY OF THE INVENTION

The object addressed by the invention is to create a device of the type in question which does not possess the disadvantages of the known devices, is especially simple and inexpensive to manufacture, and is easy to handle and safe to use.

The object according to the invention is solved by the teachings set forth herein.

The basic idea of the invention includes configuring the inventive guide device in such a manner that the guide device, together with the tubular part which serves for penetrating the stopper of a bottle, the guide device, and the supporting device, can be manufactured as one integral part. Fundamentally, for this purpose, the configuration of the holding device is as a membrane, which extends between the supporting device and the tubular part. This means that a deformation of the membrane guides the tubular part during the penetration process. Given that the membrane is tight and its edges are tightly connected to the adjacent parts, it seals the tip of the tubular part and parts adjacent to the tubular part against the environment. In addition, there are no dead spaces which could become filled with the medicine and retain a portion of the medicine. In addition, there is no danger of sucking in air and consequent foaming.

An advantageous embodiment of the device according to the invention is specified herein. In this embodiment, the membrane is formed by an expandable hose part, one edge of which is directly connected tightly to the tubular part and the other edge of which is connected tightly to the supporting device. A membrane configured in this manner is simple to manufacture, especially, for example, when it is injection-molded out of a piece of appropriately flexible plastic together with the parts adjacent to it. As will be readily apparent to a person having ordinary skill in the art, when the membrane is injection-molded, for example, it will be a continuous membrane as shown and described herein.

The diameter of the hose part is advantageously larger than the diameter of the tubular part, wherein the edge of the hose part connected to the tubular part extends toward the tubular part in a disk-shaped manner. During the penetration process, radial stresses expand or deform the disk-shaped part into the shape of a frustum in the penetration direction, wherein the hose-shaped part is deformed in the direction of the disk-shaped part and thereby becomes shorter.

According to a further embodiment, the disk-shaped part can also be configured frustum-shaped from the outset, wherein the edge of the frustum having the larger diameter is connected to the supporting device and the edge having the smaller diameter is connected to the tubular part. In this embodiment, the forces that act radially inwardly on the cylindrical part during the penetration process are reduced. This causes or supports the deformation process of the hose-shaped part.

In all cases, the tip of the tubular part is of course dimensioned in such a manner relative to the supporting device that the tip actually penetrates the stopper when it is in its forward state, thereby producing the connection to the inside of a bottle adjacent to the supporting device. Given that only the membrane and the hose-shaped part experience deformation during the penetration process, it is possible to manufacture them, together with the tubular part and the supporting part, as one piece, for example, by injection-molding a plastic that makes possible the deformation of the membrane.

An advantageous embodiment of the invention includes that the tip of the tubular part projects over a supporting surface of the supporting device in the penetration direction in such a manner that, when the device is placed on the neck of a bottle, the tip presses into the surface of the stopper without penetrating the stopper. The tubular part is therefore laterally guided not only by the membrane, but also by the tip of the tubular part, which is partially pressed into the stopper, so that the tubular part is in a parallel position, which then transitions into a parallel guide during the penetration process.

The membrane is tight around its entire perimeter. If the connecting device for connecting the inside of the tubular part to a syringe or the like is sealed with a peelable film, such as an aluminum foil, then the assembled device is sterilizable and the sterility will be maintained.

The supporting part advantageously includes a cylindrical housing part, one end of which forms a supporting surface or supporting edge for fitting into place on the mouth of a bottleneck, while the other end is fastened to the external edge of the membrane. By dimensioning the extent of the cylindrical housing part in the axial direction, a space is created into which the membrane extends in the forward position, and assumes the shape of a cone, which tapers in the penetration direction.

The membrane can also be configured stepped or undulated. To this end, the flexibility is effected by accordion-like deformation.

In an advantageous embodiment, the perimeter of the supporting device includes an edge that projects in the penetration direction for engaging the neck of a bottle and for centering. According to another embodiment of the invention, the supporting part includes snap hooks in the inside of this edge, these snap hooks allowing the part to be delivered either fully assembled on and inseparably connected to the glass bottle or to be snapped onto this bottle later.

The supporting device advantageously includes a continuous sealing lip projecting in the penetration direction for tight support on the surface of a stopper.

The connecting device for connecting the inside of the tubular part is preferably configured a conical recess or conical journal to which it is possible to connect a complementary connecting piece. The conical recess can advantageously be sealed by a peelable cover, in the form of a peelable seal for example. But it is also possible to seal the conical recess or conical journal with a sealing cap.

The tubular part can include two channels separated from one another, of which one serves as an extraction channel and one as a ventilation channel, which is connected to the environment via a lateral passageway. A filter can be advantageously arranged in the passageway. It is also advantageous for the hole or holes in the tip of the tubular part to be sealed by a cap, which is likewise penetrated when the stopper is displaced. This fitting arrangement makes it possible to preassemble the system with pre-filled syringes.

The invention will be explained in more detail based on the drawing.

BRIEF DESCRIPTION OF THE INVENTION

Figure 9:
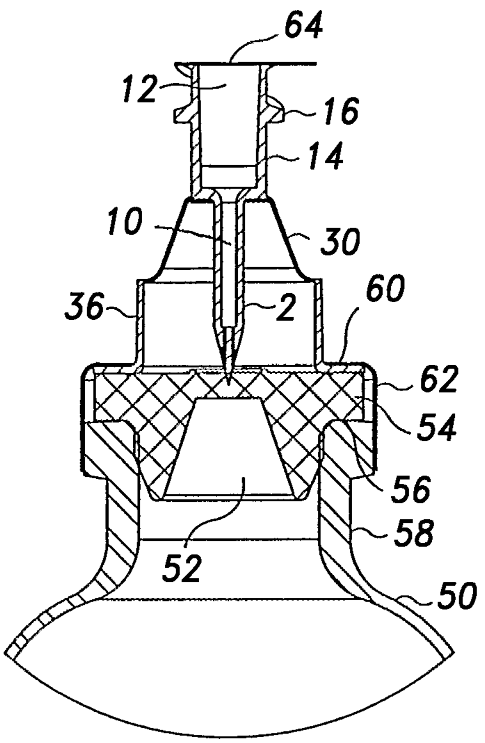
FIG. 9 depicts a modification of the embodiment of FIG. 7 on a bottle.
Figure 15:
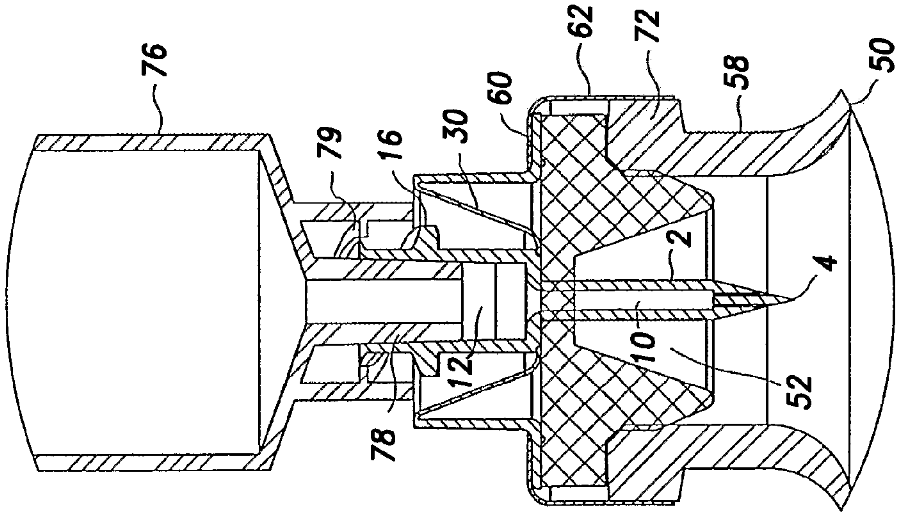
Figure 14:
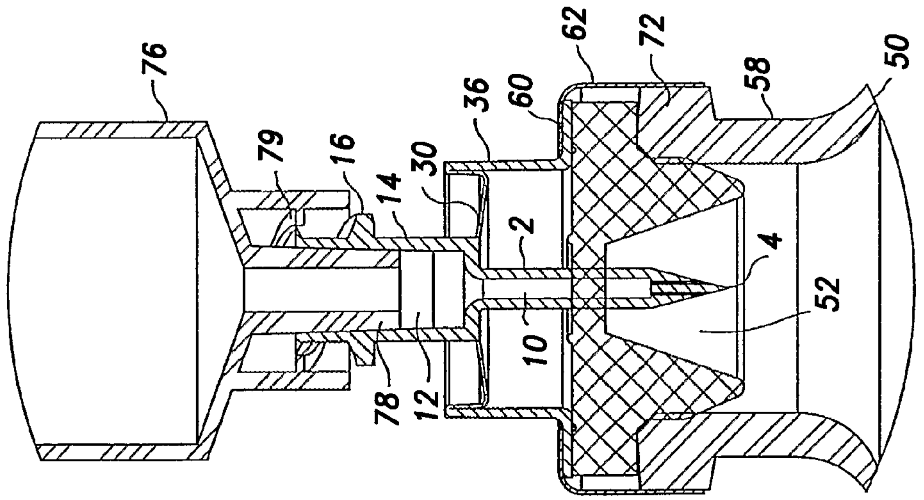
Figure 13:
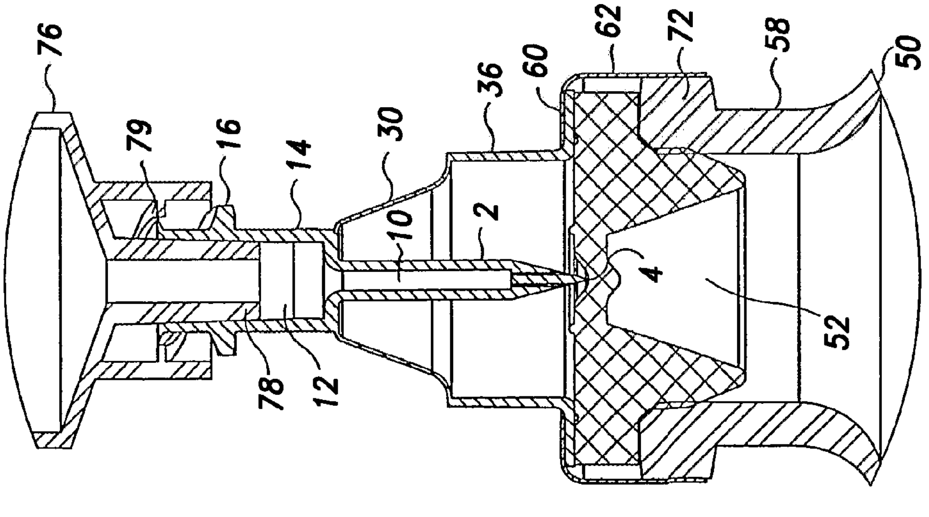
Figure 17:
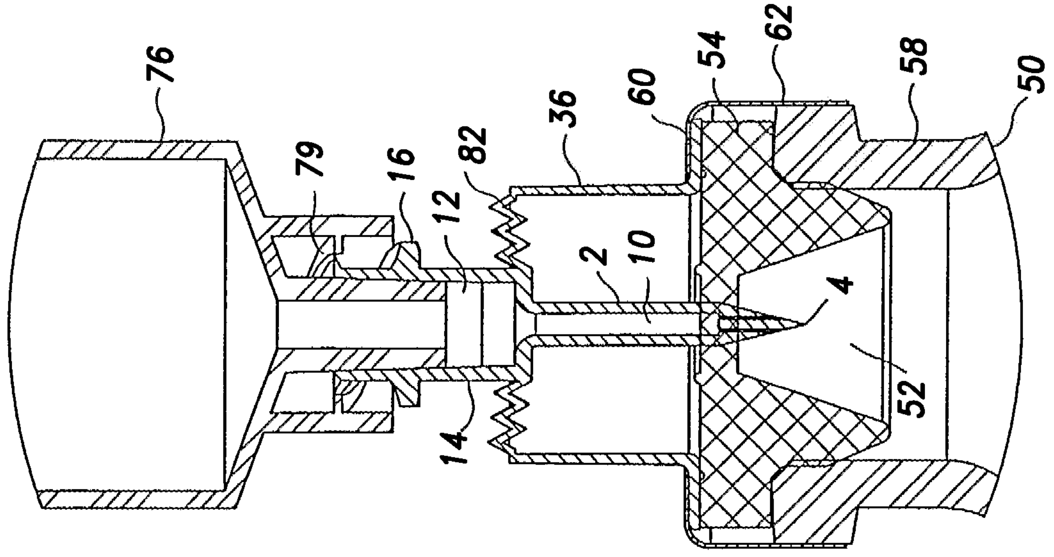
Figure 16:
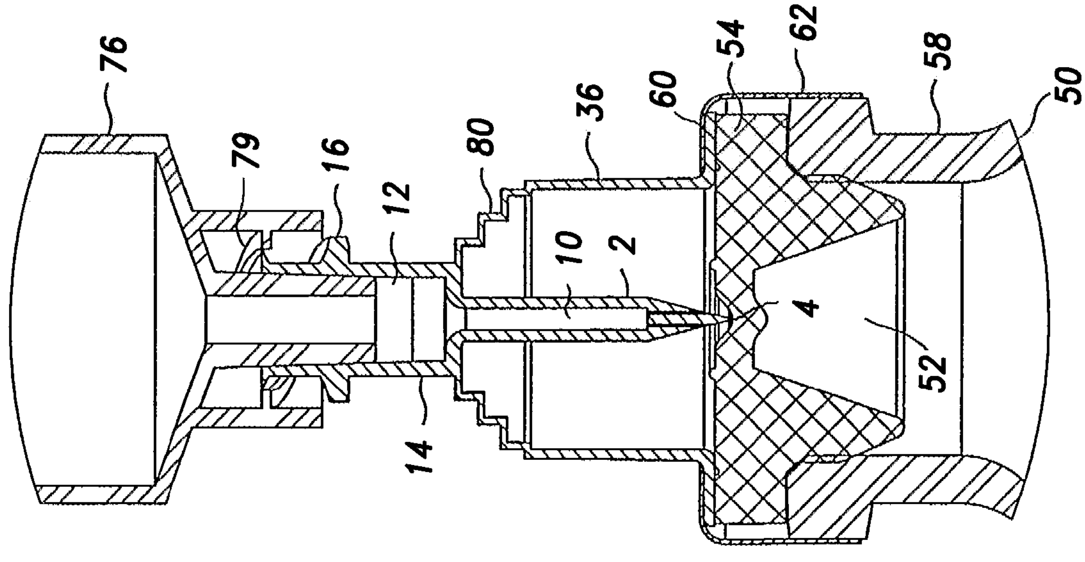
Figure 19:
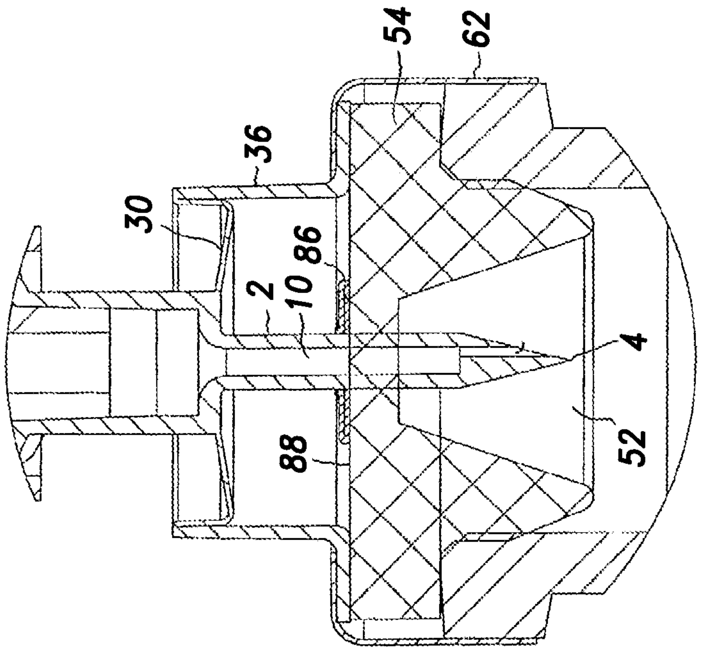
Figure 18:
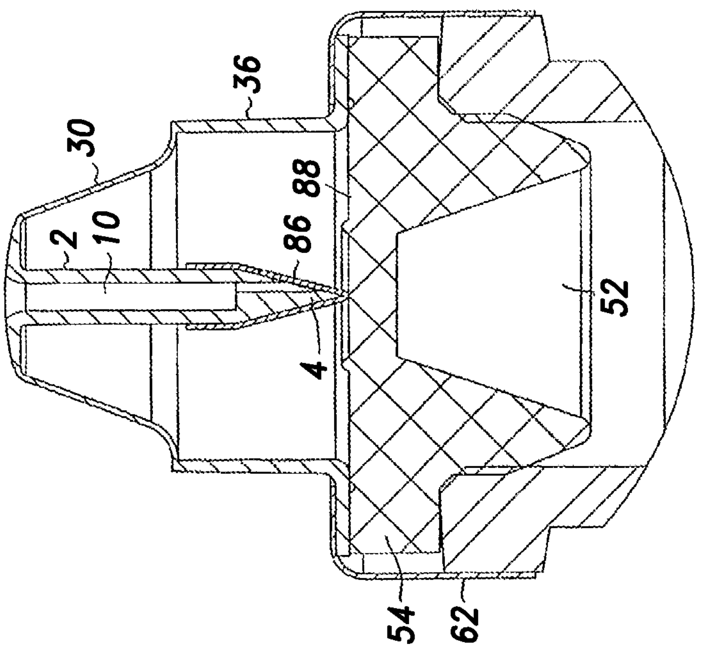

FIGS. 13, 14 and 15 explain the use of the embodiment of FIG. 9;

FIG. 16 corresponds to the illustration in FIGS. 13 and 14 and depicts a stepped membrane;

FIG. 17 depicts an embodiment with a zigzag-shaped membrane in a half-penetrated position; and FIGS. 18 and 19 illustrate the function of a cap for sealing the tip of the tubular part.

DETAILED DESCRIPTION OF THE INVENTION

Figure 1:
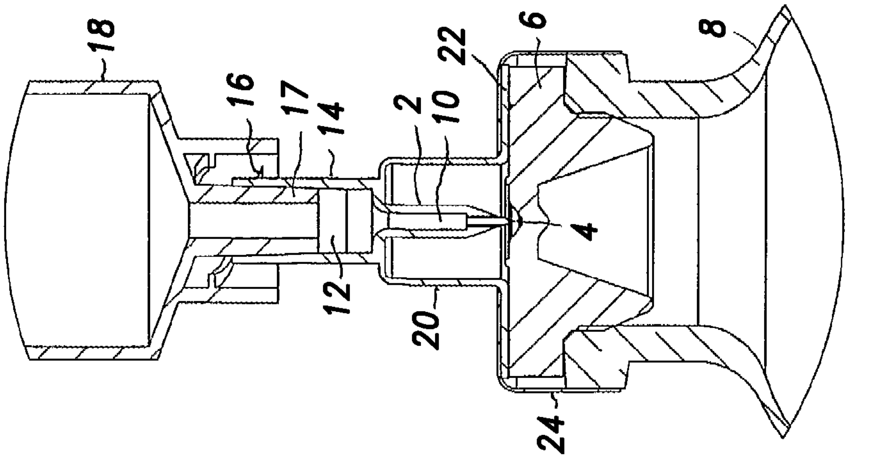
FIG. 1 depicts a first embodiment of the invention with the hose-shaped membrane.

FIG. 1 depicts a first embodiment of a device according to the invention. It includes a tubular part 2, one end of which includes a tip 4 for penetrating a stopper 6, which seals a bottle 8. An internal channel 10 of the tubular part 2 flows into a conical recess 12 for inserting a complementary conical journal 17 of a syringe 18. The conical recess 12 is disposed in a connecting part 14, on the outer surface of which an external thread 16 is disposed to tighten the syringe 18 in a known manner.

A hose part 20 extends from the connecting part 14 and a flange 22, which serves to fit and seal the stopper 6 and is held on the stopper by an aluminum crimp cap 24, is formed on the end of the hose part 20 opposite the connecting part 14. It must be noted that the tip 4 of the tubular part 2 projects over the flange 22 in the axial direction. As a result, the tip 4 presses into the stopper 6 to some extent without penetrating it when the device is put into position on the stopper 6. This causes the tubular part 2 to be twice guided laterally prior to the penetration of the stopper 6, once by the tip 4, which is partially pressed into the stopper 6 and once by the connection of the hose part 20 with the connecting part 14.

Figure 2:
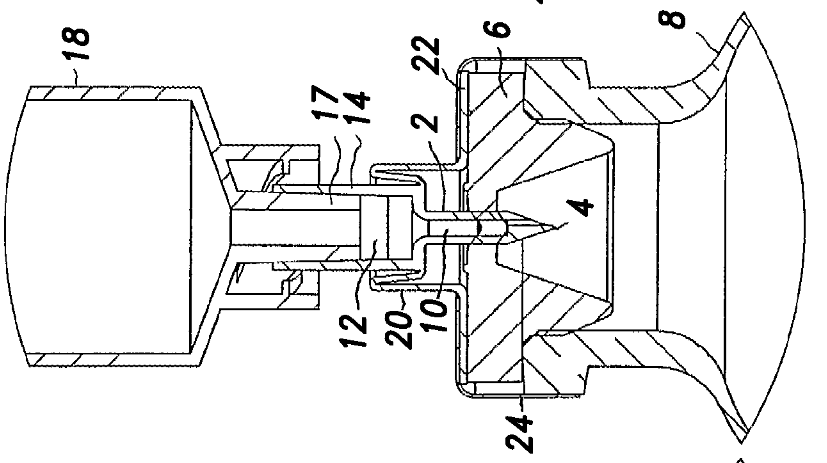
FIG. 2 depicts the embodiment of FIG. 1 with a partially penetrating tip.
Figure 3:
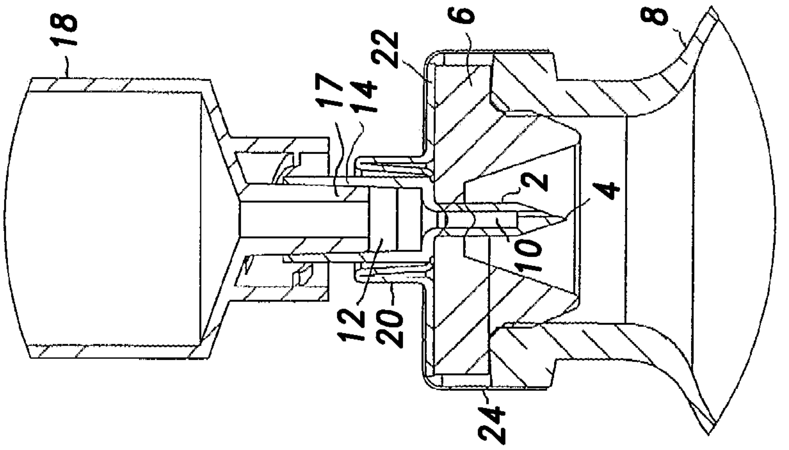
FIG. 3 depicts the embodiment of FIG. 1 with a completely penetrated tip.

FIGS. 2 and 3 explain the use of the device of FIG. 1. After the tip 18 has been connected, it is pressed in the direction of the bottle 8, thereby pushing the tubular part 2 forward in the direction of its tip 4 through the stopper 6, which seals the bottle 8. The hose part 20 is expanded by this process, as depicted in FIG. 2. Finally, the syringe is pressed further forward so that the tip 4 of the tubular part 2 projects completely into the inside of the stopper 6 and thereby into the bottle 8 when the tubular part reaches its end position. In this position, the hose part 20 is half deformed in the sense that the half adjacent to the tubular part 2 is disposed within the half connected to the flange 22.

Figures 4, 5, 6:
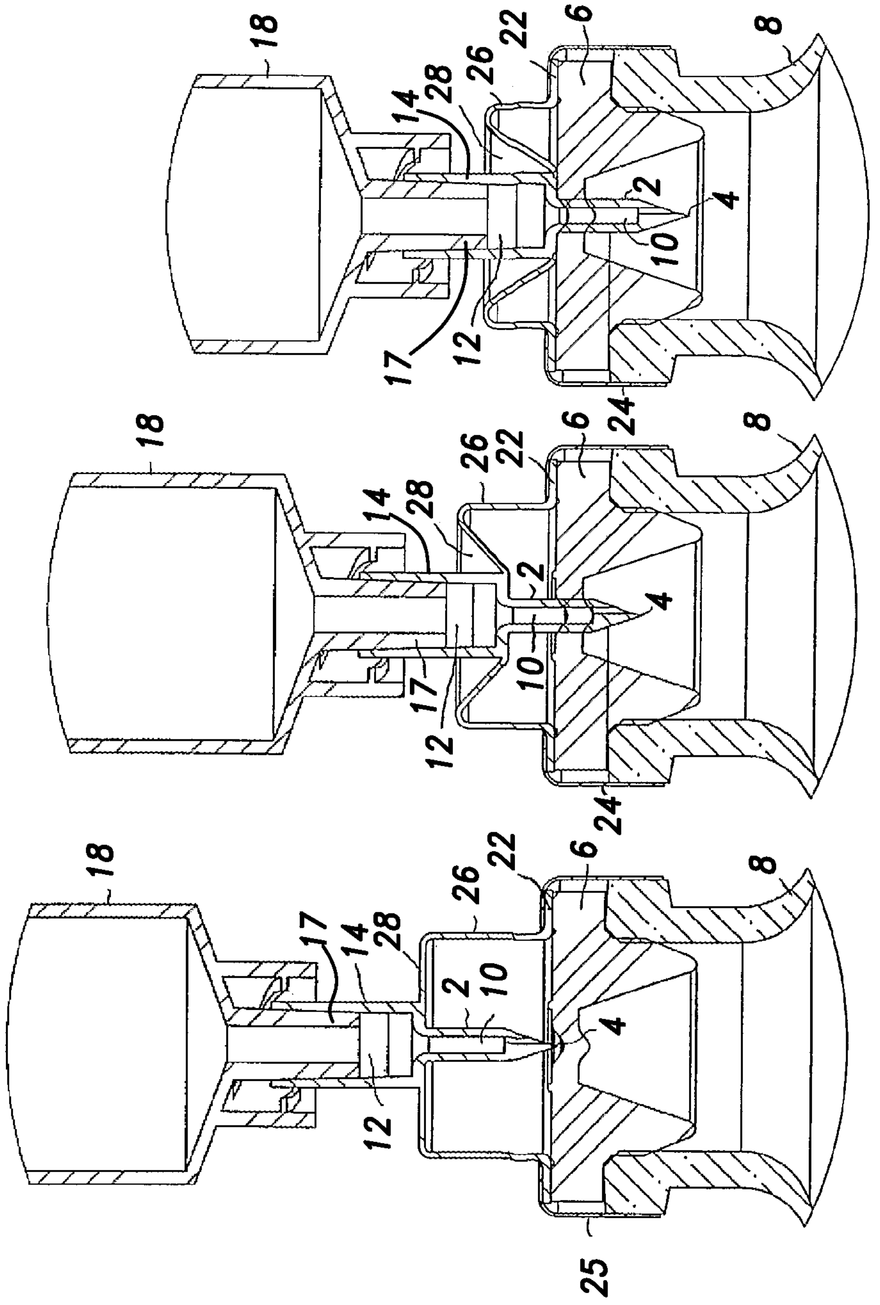
FIG. 4 depicts a modification of the embodiment of FIG. 1.
FIG. 5 depicts the embodiment of FIG. 4 with a partially penetrated tip.
FIG. 6 depicts the embodiment of FIG. 4 with a completely penetrated tip.

FIGS. 4 to 6 depict modifications of the embodiment of FIGS. 1 to 3. Identical or corresponding parts are referenced by the same reference numerals. The difference is that the diameter of a hose part 26 is substantially larger than the diameter of the tubular part 2, wherein the edge 28 connected to the tubular part 2 extends disk-shaped toward the tubular part 2. As evident from FIGS. 5 and 6, the hose part 26 and its disk-shaped edge 28 expand frustum-shaped in the penetration direction. To this end, the cylindrical part of the hose part 26 shortens itself and, in the end position of the penetration process of FIG. 6, by approximately half of its original length.

Figure 7:
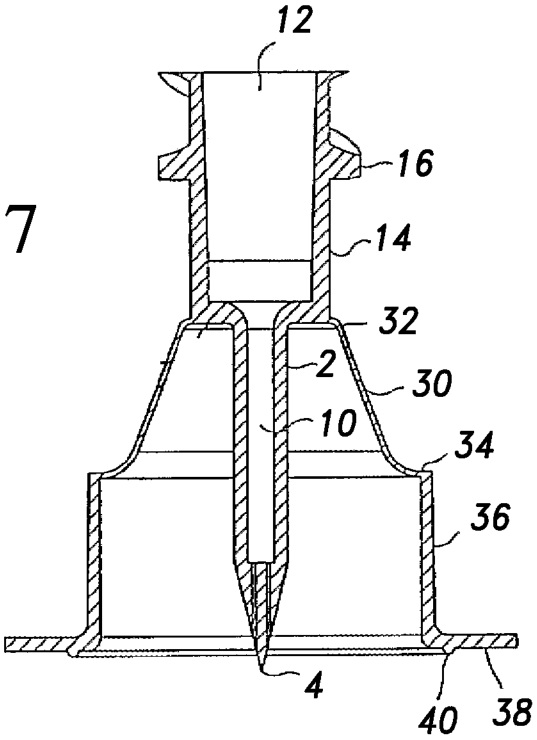
FIG. 7 depicts an embodiment with a frustum-shaped membrane on a bottle.

FIG. 7 depicts a second embodiment of the invention. Identical or corresponding parts are referenced by the same reference numerals. The essential difference to the embodiment of FIG. 1 is that the cylindrically configured hose part in the embodiment of FIG. 1 is replaced by a frustum-shaped hose part 30, the edge 32 of which is connected to the connection part 14 in the vicinity of its transition into the tubular part 2, whereas the other edge 34 transitions into a cylindrical part 36, from which a flange 38 extends for fitting into place on a stopper (not illustrated) corresponding to the stopper 6 in FIG. 1. A sealing bead 40 for a secure seal against a stopper is disposed on the flange 38.

Figure 8:
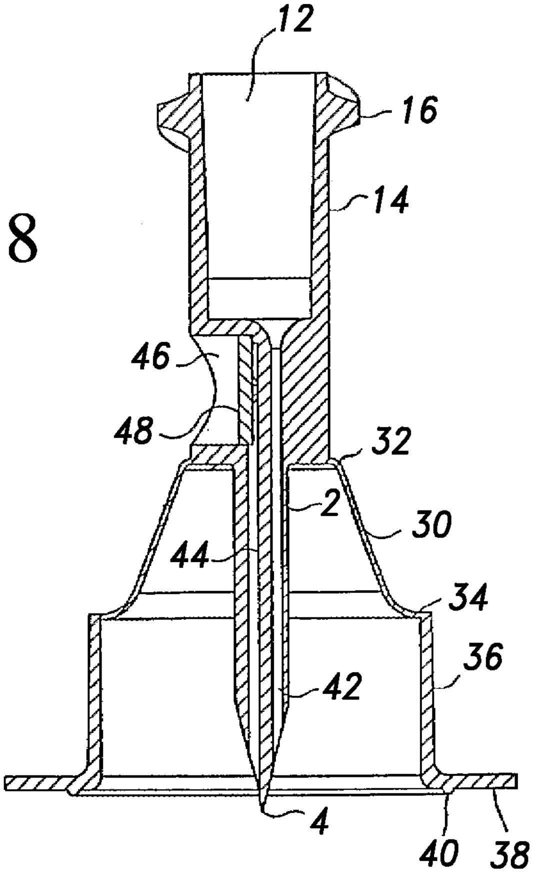
FIG. 8 depicts a modification of the embodiment of FIG. 7.

FIG. 8 depicts a modification of the embodiment of FIG. 7. Identical or corresponding parts are referenced by the same reference numerals. The difference is that a ventilation channel 44, which is connected to the environment via a lateral hole 46, is provided in the tubular part 2 next to a channel 42, which corresponds to the channel 10 in FIG. 1 and serves to conduct fluid, so that air can penetrate into the inside of the bottle. A filter 48, which is supposed to prevent the penetration of impurities from the ambient air, is arranged in the hole 46.

FIG. 9 depicts an embodiment similar to the embodiment of FIG. 7 together with the top part of a bottle 50, which is sealed by a penetrable stopper 52, the flange-like projection 54 of which rests on an edge 56 of the mouth of a bottleneck 58 of the bottle 50. An inner flange 60 of a cylindrical sheet metal part 62 made of aluminum, which is permanently dovetailed to the bottleneck 58, holds the projection 54 in this position. In this embodiment, the bottle 50 and its content, together with the device according to the invention for removing the fluid, thus form a ready-to-use object, which maintains the sterility of the spike and the inside surface of the hose part 30. A peelable seal 64 seals the inside of the connecting part 14 and the tubular part 2 to maintain the sterility.

Figure 10:
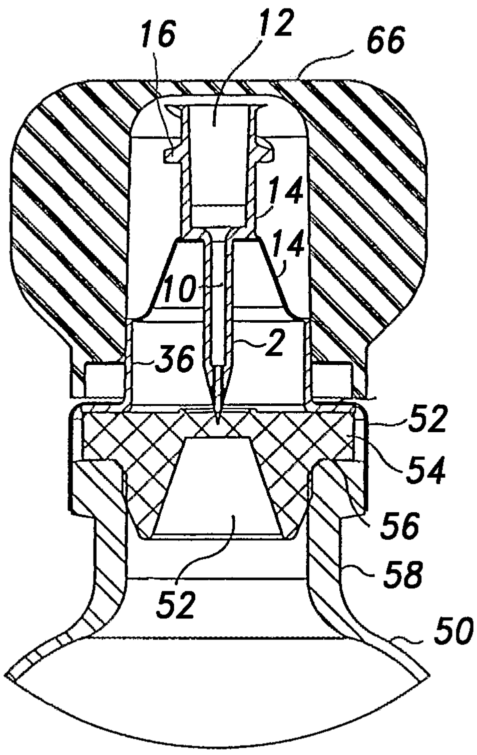
FIG. 10 depicts a modification of the embodiment of FIG. 9.

FIG. 10 depicts a modification to the embodiment of FIG. 9. The difference is that a removable cap 66, which also ensures the sterility of the exterior of the device according to the invention if it is tightly connected to the device, is put on instead of the peelable seal 64. To this end, the inner wall of the cap, which is not illustrated, can be configured conical, so that it is tightly adjacent to the cylindrical part 36 when put on.

Figure 11:
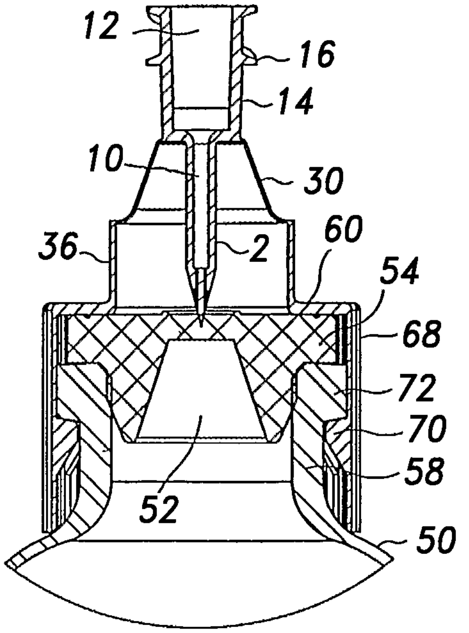
FIG. 11 depicts a further modification of the embodiment of FIG. 9 on a bottle.

FIG. 11 depicts a modification to the embodiment of the device according to the invention in the illustration of FIG. 9. Identical or corresponding parts are referenced by the same reference numerals. The difference is that a collar 68, which on its interior side includes hooks 70, which engage a continuous projection 72 of the bottleneck 58 when the device according to the invention is placed on the neck of the bottle 50 thereby tightly connecting the device according to the invention to the bottleneck 58 prior to and during use, extends from the flange 60 of the device in the axial direction. To this end, even the sheet metal part 62 for dovetailing and for secure fastening of the stopper 52 can be dispensed with. The stopper 52 for sealing the bottle 50 and the device for removing its content can therefore already be connected in a simple manner by the manufacturer.

Figure 12:
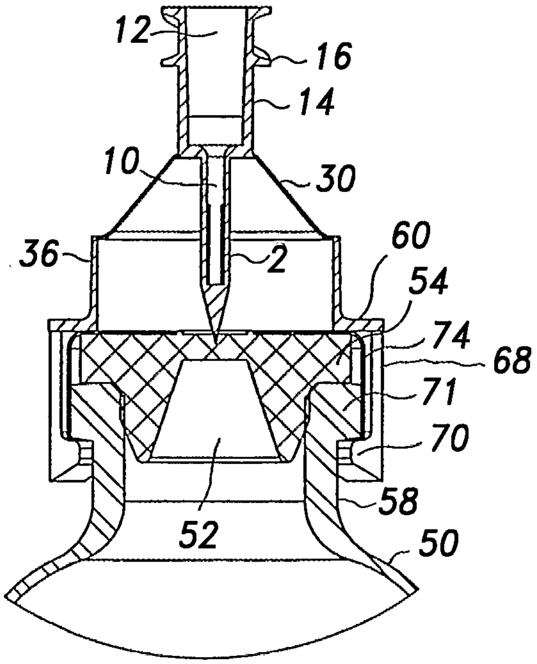
FIG. 12 depicts a modification of the embodiment of FIG. 11.

FIG. 12 depicts a modification of FIG. 11. Identical or corresponding parts are referenced by the same reference numerals. The difference is that the manufacturer has already connected the stopper 52 with its flange-like projection 54 around the bottleneck by means of a dovetailed, cylindrical sheet metal part 74.

FIGS. 13, 14 and 15 explain the use of the device according to the invention in connection with the illustration of FIG. 9. Identical or corresponding reference numerals are used in all illustrations. In FIG. 13, a syringe 76 having a conical journal 78 is inserted into the corresponding complementary conical recess 12 of the connecting part 14 and tightly connected by a screw connection of an inside thread 79 to the external thread 16. The tubular part 2 is connected to the conically tapered side of the hose part 30 and is thus laterally guided. The tip 4 of the other end of the tubular part 2 projects into the stopper 52.

FIG. 14 depicts an intermediate position of the penetration process in which the tip 4 has penetrated the stopper 52 halfway. In this position, the hose part 30 assumes a partially distorted position, partly adjoining the inside wall of the cylindrical part 36 and partly extending radially. If the tubular part is now moved further in the penetration direction, the hose-shaped part 30 will assume the shape of a frustum illustrated in FIG. 15, wherein the tapered part extends in the penetration direction. In this position, the hose part 30 is again able to apply forces in the penetration direction, holding the lower part of the connecting part 14 in a tight and standardized support on the surface of the stopper 52.

FIG. 16 depicts an embodiment similar to that of FIG. 3. Identical or corresponding parts are referenced by the same reference numerals. The difference is that the membrane is configured as a stepped annular disk 80. To this end, the steps extend ring-shaped to the tubular part 2 and are partially cylindrically parallel and centric thereto.

FIG. 17 depicts an embodiment in which the membrane is configured as an annular disk 82, which extends radially to the tubular part 2 and zigzag-shaped when the tubular part 2 has penetrated halfway as illustrated.

FIGS. 18 and 19 basically depict the top portion of the illustration of FIG. 9. Identical or corresponding parts are referenced by the same reference numerals. FIG. 18 shows that a cap 86 made of thin film seals the front outlet of channel 10. This film is penetrated when the tubular part 2 penetrates the stopper 52 and is held back by a surface 88 of the stopper 52 and pushes itself rearwards on the external surface of the tubular part 2 so that the mouth of the inner channel 10 is exposed.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

The invention claimed is:

1. Device for connecting a tubular part, the tubular part having a first end which is provided with a tip, and the tubular part having a second end which is provided with a connecting device, the connecting device being configured for connecting an inside of the tubular part with a syringe and with the inside of a bottle, which bottle includes a neck provided with a stopper which can be penetrated by the tip of the tubular part, the device comprising:

a) a supporting device for sealing and fitting the device into place on the neck of the bottle in a tight and substantially centered manner;

b) a holding device, the holding device being configured for holding the tubular part in a displaceable manner relative to the supporting device in a penetration direction of the tip of the tubular part;

c) the holding device including a tight, deformable continuous membrane with two edges, one edge of which is connected tightly to the tubular part and another edge of which is connected tightly to the supporting device; and d) the tip of the tubular part projects over a supporting surface of the supporting device in the penetration direction in such a manner that, when the device is placed on a bottleneck, in use, the tip presses into the surface of the stopper without penetrating the stopper.

2. Device according to claim 1, wherein:

a) the continuous membrane is formed by an expandable hose part, one edge of which is directly connected tightly to the tubular part, and another edge of which is connected tightly to the supporting device.

3. Device according to claim 2, wherein:

a) a diameter of the hose part is larger than a diameter of the tubular part, and an edge of the hose part is connected to the tubular part and extends toward the tubular part in a disk-shaped manner.

4. Device according to claim 2, wherein:

a) the hose part is frustum-shaped, and an edge of the frustum having the larger diameter is connected to the supporting device, and an edge having the smaller diameter is connected to the tubular part.

5. Device according to claim 1, wherein:

a) the supporting part includes a cylindrical housing part, one end of which housing part forms a supporting surface or supporting edge for fitting into place on the mouth of a bottleneck, while the hose part is connected to the other end.

6. Device according to claim 1, wherein:

a) the continuous membrane is configured as an annular disk, an inside edge of which is connected to the tubular part, and the external edge of which is connected to the supporting device.

7. Device according to claim 6, wherein:

a) the continuous membrane is configured one of stepped, zigzag-shaped, and undulated.

8. Device according to claim 1, wherein:

a) a perimeter of the supporting device includes an edge or a collar projecting in the penetration direction for engaging the neck of a bottle and for centering thereto.

9. Device according to claim 1, wherein:

a) the supporting device includes a snap edge or dovetailed edge for releasable or permanent engagement of an external projection on a mouth of the neck of the bottle.

10. Device according to claim 1, wherein:

a) the supporting device includes a continuous sealing bead projecting in the penetration direction for tightly fitting into place on the surface of the stopper.

11. Device according to claim 1, wherein:

a) the supporting device for connecting the inside of the tubular part is configured as a conical recess or conical journal for connecting a complementary connecting part.

12. Device according to claim 11, wherein:

a) the conical recess or the journal is sealed by a peelable cover.

13. Device according to claim 1, wherein:

a) the conical recess or the conical journal is sealed by a cap.

14. Device according to claim 1, wherein:

a) the tubular part includes two channels separated from one another, of which one serves as an extraction channel, and one as a ventilation channel, which is connected to the environment via a lateral hole.

15. Device according to claim 14, wherein:

a) a filter is arranged in the hole.

16. Device according to claim 1, wherein:

a) the connecting device, the supporting device, the tubular part, and the guide device form a common part.

17. Device according to claim 1, wherein:

a) the at least one hole in the tip of the tubular part is sealed by a cap.

* * * * *